United States Patent [19]
Bienhaus et al.

[11] Patent Number: 6,017,698
[45] Date of Patent: *Jan. 25, 2000

[54] METHOD OF BINDING A BIOLOGICAL MATERIAL

[75] Inventors: Gerhard Bienhaus, Wielenbach; Michael Fritz, Biblis; Jürgen Schwab, Ketsch; Edda Geisler, Mannheim; Herbert Harttig, Altrip; Heinz Macho, Fürth, all of Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/617,698

[22] Filed: Apr. 1, 1996

[30] Foreign Application Priority Data

Mar. 31, 1995 [DE] Germany ............... 295 05 652 U
Apr. 1, 1995 [DE] Germany ............... 195 12 360

[51] Int. Cl.$^7$ .................. C12Q 1/68; G01N 21/00; G01N 33/543; G01N 33/548
[52] U.S. Cl. .................. 435/6; 422/56; 422/99; 422/101; 422/255; 435/7.2; 435/7.43; 435/7.95; 435/287.2; 435/287.7; 435/287.8; 435/969; 436/518; 436/538; 436/541; 436/807
[58] Field of Search .................. 422/56–61, 99, 422/101, 255, 261; 435/6–7.2, 7.93–7.95, 287.2, 287.7, 287.8, 288.5, 969, 970; 436/518, 538, 541, 807

[56] References Cited

U.S. PATENT DOCUMENTS

| | | |
|---|---|---|
| 3,732,981 | 5/1973 | Mendelsohn .............. 210/94 |
| 3,846,077 | 11/1974 | Ohringer . |
| 3,960,727 | 6/1976 | Hochstrasser .............. 210/78 |
| 4,083,788 | 4/1978 | Ferrara . |
| 4,108,729 | 8/1978 | Mennen .............. 195/127 |
| 4,632,761 | 12/1986 | Bowers et al. .............. 210/650 |
| 4,717,653 | 1/1988 | Webster, Jr. .............. 435/5 |
| 4,780,280 | 10/1988 | Berger et al. .............. 422/56 |
| 4,787,971 | 11/1988 | Donald .............. 210/198.2 |
| 4,832,851 | 5/1989 | Bowers et al. .............. 210/650 |
| 4,909,992 | 3/1990 | Björkman . |
| 5,104,812 | 4/1992 | Kurn et al. .............. 436/165 |
| 5,124,041 | 6/1992 | Sheer et al. . |
| 5,145,789 | 9/1992 | Corti et al. .............. 436/530 |
| 5,306,622 | 4/1994 | Mangold .............. 435/7.92 |
| 5,382,408 | 1/1995 | Perlman .............. 422/102 |

FOREIGN PATENT DOCUMENTS

| | | |
|---|---|---|
| 0 378 353 | 7/1990 | European Pat. Off. . |
| 0 505 010 | 10/1991 | European Pat. Off. . |
| 91/07648 | 5/1991 | WIPO . |

OTHER PUBLICATIONS

Baxter Scientific Products, p. 948, 1991.

*Primary Examiner*—Christopher L. Chin
*Assistant Examiner*—Bao-Thuy L. Nguyen
*Attorney, Agent, or Firm*—Nikaido Marmelstein Murray & Oram, LLP.

[57] ABSTRACT

Subject matter of the invention is a method of binding a biological material to a solid phase by providing a sample liquid containing the biological material in a sample vessel (A) having an inner contour (A17); then a hollow body (C) which has a contour (C12) that matches the inner contour (A17) is introduced into the sample vessel (A) while being closed with respect to the sample vessel by means of a porous matrix (C11); the sample liquid can enter the structural form (C) through the porous matrix (C11). This method is easy to automate and reduces the generation of aerosols.

21 Claims, 3 Drawing Sheets

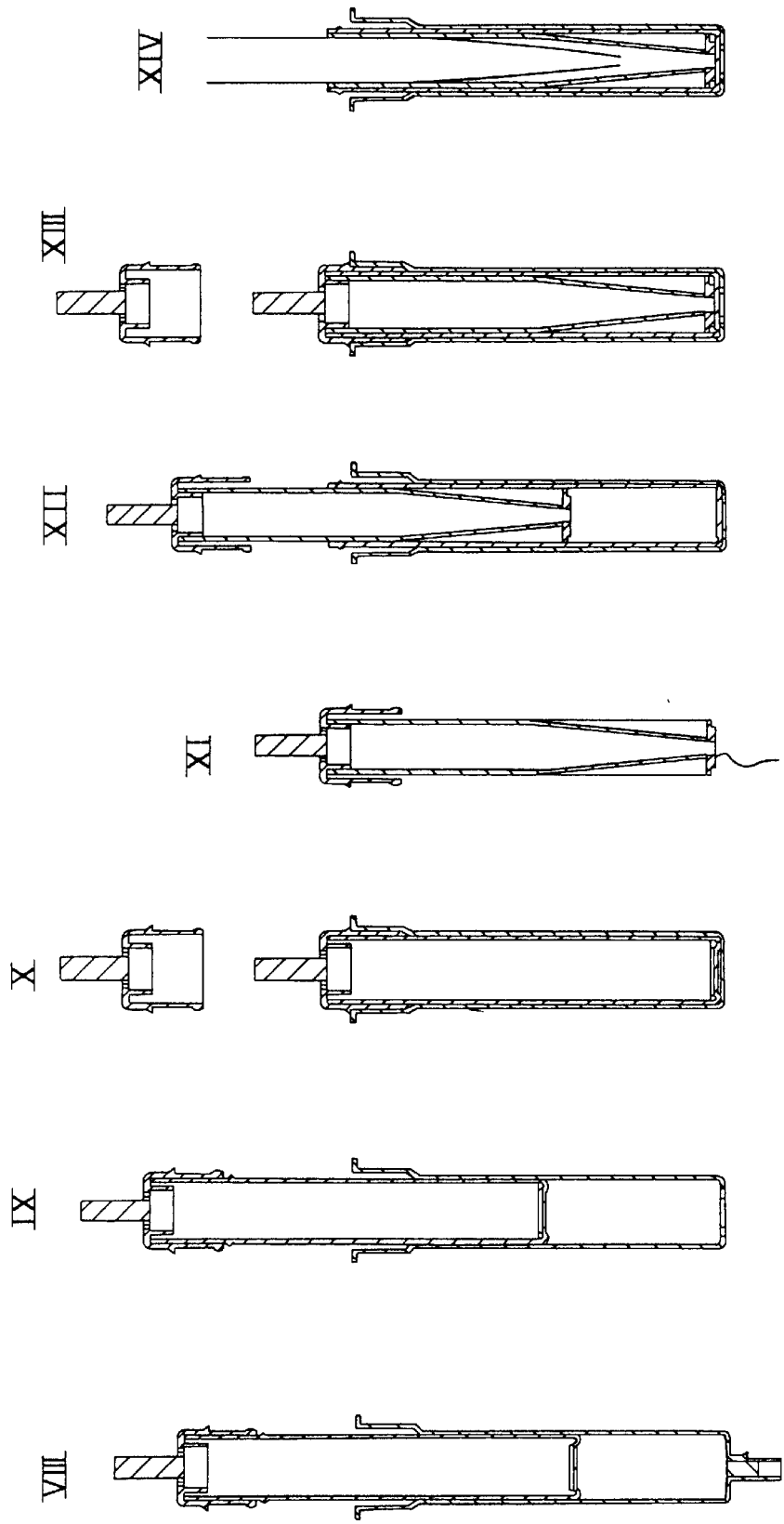

METHOD OF BINDING A BIOLOGICAL MATERIAL

Subject matter of the invention is a method of binding a biological material to a solid phase and a structural form suitable for this purpose having a porous matrix and components for connection to other functional elements.

In many fields of application, the treatment of liquids requires particular care with respect to actively avoiding contamination which could adversely affect the environment. This applies particularly to noxious liquids, but also to liquids which are used or generated in the analysis of components. The treatment steps to prepare a sample liquid for an analysis are usually carried out in the same laboratory or even the same room as the analysis itself. The use of aerosols, for example, often leads to heavy contamination of the environment with sample components; this in turn interferes with the analysis of components of other samples. An erroneous result can have terrible consequences for the patient, especially when analyzing components in the field of medical and clinical diagnostics.

Analyses that are based on the detection of nucleic acids in a sample have recently been introduced as diagnostic tools owing to their relatively high specificity. These tests are a considerable technical challenge since the contents of nucleic acids and especially the nucleic acids to be detected is a very small one while nucleic acids having similar sequences and other components which may interfere with the determination are also present in the same sample. Experience has shown that amplification procedures which have recently become more and more popular are used to produce a multitude of identical nucleic acids dependent on the presence of certain nucleic acid sequences to be tested; this greatly improves the sensitivity of the test, allowing to even detect individual nucleic acids. The risk involved in the possible high sensitivity of the tests is that contamination of other samples even with only one single nucleic acid from the environment can cause, i.e. simulate, a positive result. When using nucleic acid tests, it is therefore necessary to avoid in a particularly effective manner already the generation of contamination, i.e. the release of nucleic acids from a sample or a reaction mixture into the environment.

When preparing samples for the analysis of components, especially nucleic acids, methods have recently been used where the sample liquid and the components to be analyzed contained therein are subject to a treatment in the vessel wherein liquid is introduced into the vessel through an inlet opening and removed again through an outlet opening after undergoing one or several treatment steps. Such vessels are commercially available in the form of columns containing materials for the separation of components from the liquid, an example being the QIAamp Kit manufactured by Qiagen. These vessels are contained in another vessel, so that liquid which may leak is released into this second vessel and not into the environment. This kind of liquid treatment is, however, complex and requires a corresponding second vessel. Moreover, these vessels are used in the centrifuges in order to transfer the liquid into the second vessel.

It was, hence, an object of the present invention to partially or completely improve currently known methods for binding a biological material to a solid chase so as to avoid the disadvantages known in prior art.

Subject matter of the invention is a method for binding a biological material to a solid phase by providing a sample liquid containing the biological material in a sample vessel having an inner contour; a hollow structural form which is closed with respect to the sample vessel with the aid of a porous matrix is then introduced into said sample vessel; the vessel also has an outer contour that matches the inner contour; the sample liquid can now enter the structural form through the porous matrix.

Moreover, subject matter of the invention is also a hollow structural form containing a porous matrix capable of binding a biological material, components for attaching a lid, and a vessel which at least partially covers the structural form.

Biological material as understood in the invention can be any biological material. Said material includes in particular components of samples as they are present in the field of medical and/or clinical diagnostics or in molecular biology. Components are either low- or high-molecular components. Low-molecular components include haptens or antigens with a molecular weight of less than 2000 D. High-molecular components include in particular biopolymers, especially those that consist of amino acids or nucleotide components. The components are in particular immunologically active proteins, e.g. antigens and antibodies, and nucleic acids. The present invention is particularly suitable for the isolation of nucleic acids.

The basis for carrying out the method of the invention is the provision of a sample liquid containing the biological material. Said sample liquid is preferably contained in a sample vessel (A) having an inner contour (A17), with a smooth inner contour being preferred. In a particularly preferred case, the inside of the sample vessel has the form of a hollow cylinder.

The sample liquid can either be introduced into the sample vessel in a form that is suitable for the binding of the biological material, or it can be the result of preparative steps to which a native sample liquid is subjected. Two alternatives for preparing sample liquids containing nucleic acid containing material are described here as examples. In one embodiment, a native sample liquid is treated in a digestion vessel to release nucleic acids from cells contained therein using a reagent to lyse the cell walls. Subsequently, the nucleic acid containing sample liquid is filled into the sample vessel (A), optionally after separating undesired sample components. In a second preferred embodiment, the native sample liquid is filled into the sample vessel, and then the reagents for releasing the nucleic acids from the cells are added. In this case, the nucleic acids are also freely accessible in the sample liquid. The reaction steps necessary to prepare the biological material are known to the expert from the corresponding technical literature.

In sample vessel (A), the sample liquid containing the biological material is now brought into contact with the structural form (C) in such a manner that sample liquid enters the structural form (C) through the porous matrix (C11). The structural form is hollow allowing the sample liquid to enter therein. The structural form preferably has the form of a hollow cylinder while the end facing toward the sample vessel is closed by the porous matrix; the end facing away from the sample vessel is provided with components for attaching a lid. The outer form of the structural form matches the inner form of the sample vessel such that the structural form can be introduced into the sample vessel. In a preferred manner, the outer contour of the structural form tightly urges against the inner contour of the sample vessel so that the structural form moves inside the sample vessel like a piston.

Matrix (C11) is porous thus allowing sample liquid to pass through it. It is thus possible to use the porous matrix as a filter to avoid the penetration of undesired sample components into the structural form (C). Undesired components are particles, e.g. rests of cells walls that were not destroyed in the preceding lysis of the cell but also magnetic particles used to immobilize the cells. In this case, the sample liquid is freed from these components when passing through the porous matrix. In this case, the biological material can remain in the sample liquid. In a second function, the porous matrix itself can already be used to bind the biological material. To accomplish this, a matrix is selected which has a high affinity to the biological material to be bound. Depending on this matrix surface selected, it is possible to have either an unspecific or a specific binding. If the matrix contains antibodies on its surface, antigens directed against the antibody can be bound to the matrix (immobilized) when sample liquid passes through the matrix. Cellulose, e.g. paper, has proven to be particularly expedient as a porous matrix for the binding of immunologically active substances. Nucleic acids can also be immobilized by using a glass fleece as a matrix (sequence-unspecific immobilization) or a porous material to which there is bound a nucleic acid that is complementary to the nucleic acid to be bound (sequence-specific immobilization).

The porous matrix can either be a fleece-type matrix or a particle-type matrix; the latter must be located in the structural form, e.g. by means of a filter, such that it is possible for the sample liquid to enter the pores of the particle-type matrix. In the preferred case, the porous matrix is a fleece-type matrix. It is also possible to use a matrix consisting of several components (e.g. fleeces with a varying degree of flexibility). Due to the porous nature of the matrix, the liquids pass slowly through the matrix so as to allow a particularly effective reaction, e.g. binding liquid components to the matrix.

The matrix is attached to the structural form in a known manner. It can, for example, be inserted into the structural form at the side facing away from the sample vessel, and fixed in a given position with the aid of a ring. In addition, the matrix can also be sealed in the structural form. In a preferred manner, however, the matrix is included in the structural form on the side facing toward the sample vessel, preferably in a preinstalled ring along the inner wall of the structural form; subsequently, the overlapping rim is crimped toward the inside such that the matrix is fixed in its position between the ring and the crimped edge.

In a particularly preferred manner, the matrix is held on the side facing away from the sample vessel by an annular circumferential projection in the inner contour of the structural form. In a most particularly preferred manner, the thickness of said projection is selected such that it can be broken off without destroying the matrix and the remaining structural form.

Moreover, it is preferred that the porous matrix be compressible. A compressible matrix as understood in the invention is one where the outer volume of the matrix is reduced when pressure is applied with the aid of a stamp-type device; the pore sizes are then also reduced, so that the liquid contained in the matrix is pressed out of these pores.

In a preferred embodiment, the structural form (C) is introduced into the sample vessel (A) with the aid of a lid which allows an aerosol-tight seal of he structural form with respect to the environment. By providing matching contours the sample liquid is forced to pass through the porous matrix into the inside of the structural form. The biological material is thus bound to the porous matrix. Subsequently, the sample liquid that was purified with respect to the biological material is removed from the structural form and/or the sample vessel. This can be accomplished in that residual liquid is removed from the structural form at the side facing away from the sample vessel, e.g. by means of pipetting. It is, however, preferred that residual liquid be removed from the sample vessel (A) (e.g. by drawing off) and that residual liquid which has entered the structural form during this process pass through the porous matrix and into the sample vessel.

The method of the invention exhibits particular advantages for those biological materials where one single passage through the porous matrix is not sufficient to completely bind the total amount of biological material. With the design of the invention it is possible to allow the sample liquid to pass through the porous matrix another two times; this is accomplished by retracting the structural form, e.g. into a part of the sample vessel that is not filled with sample liquid, and inserting it again into the part of the sample vessel which is filled with liquid. This can increase the yield of immobilized biological material.

After removing the residual sample liquid from the pores of the matrix, the latter can be treated with the washing solution in order to remove all other residual contamination that may still be present. In accordance with the invention this is accomplished when the structural form is still inside the sample vessel. By selecting a lid, which provides an aerosol-tight seal of both sample vessel and structural form, the amount of contaminating aerosols which can enter the structural form is reduced. For a particular expedient treatment of the structural form and the sample vessel, the force necessary to remove lid (B) from sample vessel (A) should be smaller than the force necessary to remove lid (B) from structural form (C). This can be accomplished in that the pressure exerted on the lid is different for those two components. Said pressure can be adjusted by providing corresponding snap-in elements.

Moreover, by providing snap-in elements in the structural form (C) and the sample vessel (A), it is possible to remove the lid without removing the structural form from the sample vessel.

Provided the biological material is bound to the porous matrix, it can be further treated either inside the sample vessel (A) or after removing the structural form (C) from said sample vessel (A). Continued treatment includes in particular the release of the binding of the biological material to the porous matrix. It is, however, also possible to directly detect the biological material when it is bound to the porous matrix.

The sequence of carrying out the two steps of providing the sample liquid in the sample vessel (A) and inserting a structural form into the sample vessel can principally be selected as desired. In a first option, the structural form is inserted into the sample vessel and subsequently the sample liquid is filled in. The liquid can be filled into the inside of the structural form, but also into the sample vessel. In the preferred case, the sample liquid is first introduced into the sample vessel and subsequently, the structural form is introduced into the sample vessel.

As opposed to methods that are based on passing a sample liquid through a porous matrix by means of suction, e.g. a column material, or on passing the sample liquid through the porous membrane by means of centrifugation, the method of the invention has the advantage of generating significantly less aerosols; also, centrifugation and suction are rather complex procedures. With the method of the invention it is also possible to automate the operating steps in a more efficient manner than with known methods. The possibility of passing the sample liquid several times through the porous matrix is yet another significant advantage of the method.

FIG. 1 shows a structural form in accordance with the invention. It is essentially a hollow cylinder which has a porous matrix (C11) on the side facing toward the sample vessel. Said matrix is fixed in its position by ring (C18) and the crimped edge. Moreover, the circumferential holding means (C15 and C13) to attach a lid and/or the structural form in an elution vessel can also be seen. In a preferred manner, the structural form also contains additional means for attaching other additional means in its interior, e.g. a snap-in notch (C17) to mount a stamp. The structural form has an outer contour (C12) and an inner contour (C16). The hollow space in the interior of the structural form is designated as C14. The ring (C18) is shown in a form which allows it to be broken off the structural form in that a desired breaking point is provided alone the inner contour. Matrix (C11) is preferably a compressible material. Compression is achieved with the aid of the stamp (E) that is introduced into the structural form. The compressed matrix is fixed in position with the aid of a stamp (E) and suitable projections at the outer contour and allowing the stamp to snap in the notch (C17). The circumferential edge (C19) can be used as a sealing lip with respect to the inner contour of an elution vessel (D). Elution liquid prepared for use in the process is thus prevented to escape between the outer contour (C12) of the structural form and the inner contour of the elution vessel. The sealing lip can assume the same function to allow the sample liquid to completely pass through the porous matrix (C11) with respect to the inner contour of the sample vessel (A).

In a particular embodiment of the method of the invention for processing nucleic acid-containing sample solution, the following operating steps are carried out (see FIG. 2). In a first step (I) a cell-containing sample liquid is incubated in a sample vessel (A) with a material to which the cells are bound in order to obtain the nucleic acids. To accomplish this, said material can either exhibit specific binding properties for the surface of the cells, e.g. by immobilizing antibodies to surface antigens or an absorber material (A16, not shown); it is, however, also possible to provide a material with filter properties (A15, not shown) which retains the cells when liquid passes through the material, e.g. when removed from the sample vessel. Conditions for immobilizing cells on surfaces are known to the expert, e.g. from Methods in Enzymology, vol. 171, Biomembranes/Part R Transport Theory: Cell and Model Membranes, edited by Sidney Fieischer, Becca Fieischer, Department of Molecular Biology, Vanderbilt University, Nashville, Tenn.

During incubation, a lid (B) preferably closes the sample vessel to ensure active and passive protection from contamination.

In another step, the liquid is removed from the sample vessel while cells whose nucleic acids are to be isolated remain in the vessel where they are bound to the material. If the cell-binding material is a particle-type material, the cells can be retained in that the material is magnetic and a magnetic field is applied to the sample vessel from the outside; said field has to be strong enough to retain the particle-type material in the sample vessel when the liquid is removed. The liquid can be removed in different ways. It is, for example, possible to remove the liquid through an outlet opening (A11) which is spatially separated from the inlet opening (A10). If said outlet opening is located in a lower part of the sample vessel and below the retained cells, the liquid can be drawn off, e.g. by applying a minor vacuum. To accomplish this, a valve may be provided at the outlet opening to generate such a low pressure.

In order to remove other potentially interfering sample components from the cells, it is possible to provide one or several washing steps. To achieve this, washing liquid is filled into the sample vessel; said washing liquid dissolves possible contamination which, however, does not essentially affect the binding of the cells to the surface of the cell-binding material. Such washing solutions are known to the expert, e.g. from cell-separation protocols or corresponding cleaning kit protocols for nucleic acids. They basically depend on how the cells bind to the material.

After the last washing solution has been removed from the sample vessel (A), the purified, enriched cells are brought into contact with a suitable lysis liquid to release the nucleic acids from the cells. The reagents of this lysis solution largely depend on the type of immobilized cells. If the cells are bacteria, the lysis solution preferably contains proteinase K to digest the cell walls. Optionally, the lysis can be supported by hearing or cooling and agitating the reaction mixture. If magnetic particles are used as cell-binding material, the mixing can also be accomplished with the aid of a magnet. Moreover, it is possible to mix the solution by shaking the sample vessel. Once digestion is completed, the nucleic acids to be isolated are freely accessible in the solution.

Even during lysis, it is preferred that the reaction vessel be closed by a lid in order to avoid contamination from the environment. After completion of the lysis, the lid is removed, preferably with the aid of a corresponding mechanical device. Subsequently, a structural form (C), whose outer contour (C12) matches the inner contour (A17) of the sample vessel, is introduced into the sample vessel which contains a mixture of digestion products of the cells and the nucleic acids. This structural form is hollow and sealed toward the sample vessel and toward the reaction mixture by means of a filter. The introduction of the structural form (C) is preferably accomplished with the aid of a component (B11) of lid (B) which also contains a component (B10) suitable to close the sample vessel. In this case, the structural form is taken up with the aid of a lid (II) and introduced in the sample vessel while the latter is closed. During this procedure, the reaction mixture can enter the hollow space (C14) of the structural form across filter (C11) (IV). By providing a filter, it is possible to prevent large particles from entering into the hollow space; if the filter already has nucleic acid binding properties, the nucleic acid can already be bound to the filter while the reaction mixture is passing through. In this case, it is expedient to select a glass fiber containing filter material.

In the next step, the remaining lysis reaction mixture is removed from the device consisting of A and C, e.g. by drawing off solution from the sample vessel through an outlet opening (A11) located in the lower portion of the vessel. The solution that has entered the hollow body (C14) of the structural form is, hence, also removed so that the filter more or less no longer contains any liquid. Subsequently, the so far used lid (B) is removed while the structural form (C) still remains in the sample vessel (where it is snapped into position) (V).

Simultaneously or subsequently, an elution vessel (D) is prepared to receive the structural form (C). A lid that can be provided on this vessel, if necessary is removed (VI). Preferably, an elution solution is provided, e.g. by pipetting, in the elution vessel prior to transferring the structural form (C) into the elution vessel (D). The composition of the elution solution depends on how the nucleic acid is bound to the material in filter (C). It contains reagents which cause the immobilized nucleic acids to elute from the material, i.e. to be released therefrom. Lid (B) initially used to close the elution vessel, is now placed onto the sample vessel (A) with the structural form (C) (VII).

In order to remove the structural form (C) from sample vessel (A), the structural form (C) is removed with the aid of the lid (VIII). The combination of lid and structural form is subsequently introduced into the elution vessel (IX). In a preferred manner, the structural form (C) contains a means (C13k, not shown) to fix the structural form in position in the elution vessel (D). Owing to sad means, the structural form (C) or the vessel (D) have to be destroyed in order to remove said structural form, or a force has to be applied which exceeds the force necessary to remove the lid (B) from structural form (C). The invention does not propose to remove the structural form from the elution vessel.

While the structural form (C) enters the elution vessel, the already provided elution solution enters filter (C11) to release the immobilized nucleic acid from the solid matrix. Depending on the amount of prepared elution solution, either only the filter is impregnated with the elution solution or the elution solution enters the hollow body (C14) together with a released nucleic acid. For complete elution of the nucleic acids, the inner contour of the elution vessel should be configured to urge as tightly as possible against the outer contour of the structural form.

In a subsequent step, lid (B) is removed from the combination of structural form (C) and elution vessel (D) (X). Said lid (B) is used to take up a stamp (E) (XI) and introduce said stamp (E) into the hollow space of the structural form (C) (XII). Said lid engages stamp (E) in the inside. The stamp is pressed against the filter (C11) such that liquid which is present in the filter passes through an opening located in the contact pressure surface into the interior of the stamp. This procedure is particularly effective when the outer contour of the contact pressure surface matches the inner contour of the structural form (C) in at least the area where said pressing is accomplished. Stamp (E) can preferably be fixed in this position, e.g. by allowing it to snap into position. Since the so formed device is relatively well sealed by means of the lid, the nucleic acid containing solution can be stored in the device.

In order to remove the desired amount of nucleic acid solution, the lid can be removed (XIII) and the desired amount can be taken out via an opening in the interior of the stamp, e.g. by means of pipetting (XIV). Subsequently, the lid can be placed back into position.

Another subject matter of the invention is a hollow structural form containing a porous matrix (C11) capable of binding a biological material, and components (C12, C13) to attach a lid and a vessel (D) which at least partially surrounds the structural form. The components (C12 and C13) are preferably snap-in-type elements to improve the handling of the structural form and facilitate the interaction of the individual modules.

The structural form in accordance with the invention can be manufactured in a simple manner by means of injection molding. The base is preferably made of plastic, such as polypropylene.

Figure 1:
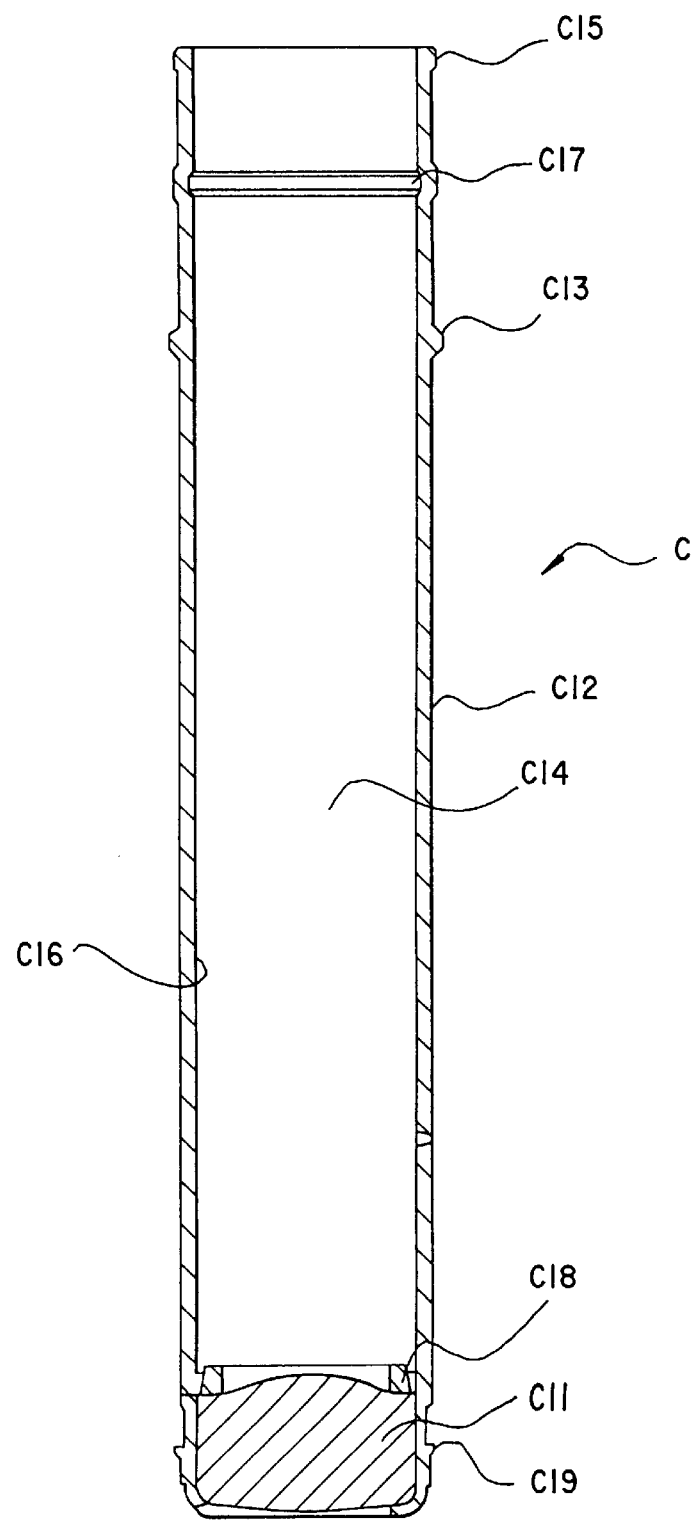
FIG. 1 is a longitudinal section of the structural form in accordance with the invention.
Figures 2A, 2B, 2C, 2D, 2E, 2F, 2G:
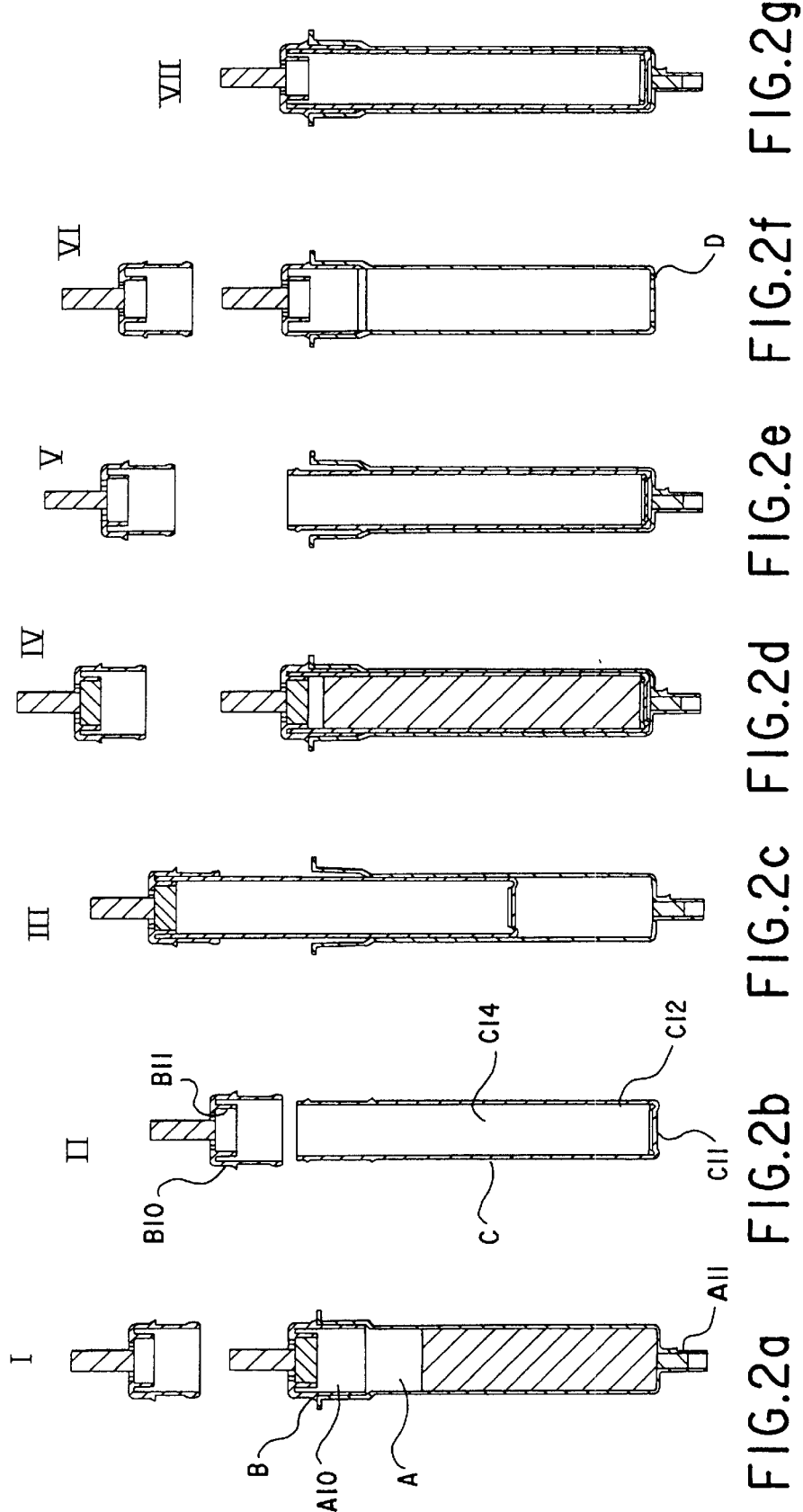
FIG. 2 shows a method for isolating nucleic acids comprising the method of the invention for binding a biological material to a solid phase.

The following examples are given to further illustrate the invention in greater detail:

EXAMPLE 1

The example of a structural form in accordance with the invention is a cylindrical plastic tube (outer diameter=6.75 mm, inner diameter=6.0 mm, height=40.4 mm. Novolen 1100 UCX, manufactured by means of injection molding); its upper inlet opening at the outer wall is provided with a snap-in lip (C15) for reversibly coupling a lid to the structural form. Another snap-in lip (C13) is located approximately 6 mm below the first snap-in lip. It is used for the irreversible positioning of the structural form in the elution vessel (D). A snap-in notch (C17) is provided at the upper inlet opening at the inner wall in order to irreversibly position a pressing stamp (E) in the interior of the structural form.

The outlet opening (=bottom of tube) is closed with a glass fiber fleece (diameter=7.0 mm, height 1.5 to 3.0 mm).

Toward the top, the glass fiber fleece is positioned with the aid of a ring (C18) which is connected to the inner wall of the tube at three sites; from the bottom, it is positioned via a crimped edge. The circumferential ring which can be torn off is advantageous to minimize the dead volume. It satisfies the following requirements: fixing the one or two layers of glass fiber fleece at the top; when pressing out the glass fiber fleece with the pressing device, it should break off and hence minimize the play. At the outer surface, provision is made for sealing lips (C19) which act as seals between structural form and sample vessel (A) and/or elution vessel (D).

EXAMPLE 2

Biological materials/chemicals/devices

| Sample material: | Longitudinal standard II, Boehringer Mannheim |
|---|---|
| Binding buffer: | Qiagen AL 1/AL 2 (4 parts/1 part), manufactured by Qiagen |
| Washing buffer: | Qiagen AW buffer, manufactured by Qiagen |
| Elution buffer: | 10 mM Tris buffer pH 9.0 |

Sample vessel (A)
Lid of sample vessel (B)
Structural form (C) having a porous matrix made of a glass fleece (C11)
Elution vessel (D)
Lid of elution vessel (E)
Pressing stamp of structural form (F)
Preparing the sample solutions

| Sample: | 200 µl | (6 µl longitudinal standard II dissolved in PBS buffer |
|---|---|---|
| Proteinase K | 25 µl | |
| Binding buffer | 200 µl | (AL 1 and AL 2 buffer mixed in a ratio of 4 + 1) |
| Ethanol | 210 µl | |
| Total volume each batch: | 635 µl | |

How an example is carried out

Sample vessel (A) is filled with 200 µl of sample, 25 µl of proteinase K solution and 200 µl of binding buffer. Sample vessel (A) is closed with lid (B) of the sample vessel. The liquids are mixed in the closed vessel. Subsequently, the mixture is incubated at 70° C. for 10 min (digestion of cells), followed by a cooling phase where it is cooled down to 20° C. in 3 minutes. Sample vessel (A) is opened, and 210 µl of ethanol are added. Sample vessel (A) is closed, and the solution is mixed.

Sample vessel (A) is opened. The lid (B) of the sample vessel is used to get the structural form (C) with a porous matrix out of its support. The structural form with the glass fleece matrix is introduced into the sample vessel which is filled with liquid through the inlet opening. While being introduced, the liquid present in the sample vessel (A) passes through the glass fleece from the bottom. The freely moving nucleic acid now binds to the glass fleece matrix. In the next step, the liquid present in the structural form (C) is drawn off towards the bottom. The liquid again passes through the glass fleece and nucleic acid which is not yet bound is now immobilized on the matrix.

The glass fleece matrix is washed twice with 500 μl of washing buffer. The buffer solution above the matrix is drawn off through the glass fleece. Subsequently, the matrix is dried with a purified nucleic acid at 50° C. for 3 minutes Lid (B) of the sample vessel is discarded.

Using lid (B) of the elution vessel, the structural form (C) containing the nucleic acid is transferred from the sample vessel (D) into a prepared elution buffer with 200 μl elution buffer in it. The elution buffer releases the nucleic, acid from the glass fleece matrix. The nucleic acid is partially located above the matrix.

By introducing a pressing stamp (E) with the aid of the lid (B) of the elution vessel, the matrix in the structural form is compressed in order to minimize the dead volume of the nucleic acid solution.

Nucleic acid yields

The tests were carried out with two different nucleic acid sample concentrations. The following results could be determined:

Test series 1: Sample concentration: 6 μg of nucleic acid/200 μl elution solution

| Test number | Isolated bound nucleic acid (μg) | Yield (%) |
| --- | --- | --- |
| Test 1 | 1.4 μg | 22.9 |
| Test 2 | 1.6 μg | 27.5 |
| Test 3 | 1.2 μg | 23.8 |
| Test 4 | 1.5 μg | 29.8 |
| Test 5 | 1.6 μg | 35.2 |

Test series 2: Sample concentration: 20 μg of nucleic acid/ 200 μl elution solution

| Test number | Isolated bound nucleic acid (μg) | Yield (%) |
| --- | --- | --- |
| Test 1 | 3.7 μg | 28.0 |
| Test 2 | 6.4 μg | 38.8 |
| Test 3 | 4.8 μg | 49.0 |
| Test 4 | 4.1 μg | 30.3 |
| Test 5 | 5.1 μg | 37.8 |

LIST OF REFERENCE NUMERALS

A Sample vessel
10 Inlet opening
11 Outlet opening
17 Inner form
19 Outer form
22 Element to position additional functional elements
B Lid
10 Component to close sample vessel A
11 Component to handle structural form C
C Structural form
11 Porous matrix
12 Outer contour
13 Means for fixing the structural form in the elution vessel
14 Hollow body
15 Means for positioning lids
16 Inner contour
17 Means for positioning stamp E, circumferential
18 Circumferential break-away bar
19 Edge
D Elution vessel
12 Snap-in notch
E Stamp
10 Contact pressure surface
11 Outer contour
12 Interior
13 Opening in contact pressure surface
14 Removal opening
15 Seal
16 Snap-in ring
17 Recess

We claim:

1. A method of removing a biological material from a sample liquid, comprising:
    (a) providing a sample liquid containing the biological material in a sample vessel having an inner contour surface;
    (b) binding the biological material to a porous matrix by inserting a first end of a hollow structural form into the sample vessel and contacting the hollow structural form and the sample liquid within the sample vessel, the hollow structural form
        having an outer contour surface which corresponds to the inner contour surface of the sample vessel such that the outer contour surface of the hollow structural form urges against the inner contour surface of the sample vessel when the inner contour surface of the sample vessel and the outer contour surface of the hollow structural form are in contact,
        having at least one opening located to permit the passing of the sample liquid from the exterior of the hollow structural form to the interior of the hollow structural form, and
        comprising the porous matrix, the porous matrix located such that the sample liquid passing through the at least one opening passes through the porous matrix to reach the interior of the hollow structural form,
    (c) separating the sample liquid from the hollow structural form comprising the porous matrix having the biological material bound thereto by removing the sample liquid at least once through the porous matrix; and thereafter
    (d) releasing the biological material from the porous matrix.

2. The method of claim 1, wherein when the inner contour surface of the sample vessel and the outer contour surface of the hollow structural form are in contact, the outer contour surface of the hollow structural form urges against the inner contour surface of the sample vessel to form a liquid-sealing relationship.

3. The method of claim 1, wherein the at least one opening is located proximate to the first end of the hollow structural form.

4. The method of claim 1, wherein the porous matrix is located in the at least one opening.

5. The method of claim 1, wherein the porous matrix is a glass fleece matrix.

6. The method of claim 1, wherein the biological material is a nucleic acid.

7. The method of claim 1, further comprising, after step (b), retracting the hollow structural form to a part of the sample vessel which is devoid of sample liquid, and again contacting the hollow structural form and the sample liquid within the sample vessel to bind any unbound biological material to the porous matrix.

8. The method of claim 1, wherein the sample liquid is provided in the sample vessel before the sample vessel and the hollow structural form are contacted.

9. The method of claim 1, wherein the hollow structural form further comprises a lid which allows a gas-tight seal of the hollow structural form.

10. The method of claim 1, wherein in step (c) the sample liquid is separated from the hollow structural form by drawing off the sample liquid using pressure.

11. A method of detecting the presence of a biological material in a sample liquid, comprising:

(a) providing the sample liquid containing the biological material in a sample vessel having an inner contour surface;

(b) binding the biological material to a porous matrix by inserting a first end of a hollow structural form into the sample vessel and contacting the hollow structural form and the sample liquid within the sample vessel, the hollow structural form having an outer contour surface which corresponds to the inner contour surface of the sample vessel such that the outer contour surface of the hollow structural form urges against the inner contour surface of the sample vessel when the inner contour surface of the sample vessel and the outer contour surface of the hollow structural form are in contact, having at least one opening located to permit the passing of the sample liquid from the exterior of the hollow structural form to the interior of the hollow structural form, and comprising the porous matrix, the porous matrix located such that the sample liquid passing through the at least one opening passes through the porous matrix to reach the interior of the hollow structural form;

(c) separating the sample liquid from the hollow structural form comprising the porous matrix having the biological material bound thereto by removing the sample liquid at least once through the porous matrix;

(d) releasing the biological material from the porous matrix; and thereafter (e) detecting the biological material.

12. The method of claim 11, wherein the porous matrix is a glass fleece matrix.

13. The method of claim 11, wherein the biological material is a nucleic acid.

14. The method of claim 11, further comprising, after step (c), separating the hollow structural form and the sample vessel.

15. The method of claim 11, wherein the biological material is released from the porous matrix using an elution solution.

16. The method of claim 11, further comprising, after said releasing step, removing the biological material from the hollow structural form.

17. The method of claim 16, wherein said removing step comprises contacting a stamp, having an opening adjoining a hollow interior, with the porous matrix, and applying pressure to the porous matrix using the stamp, whereby the biological material passes through the opening into the hollow interior of the stamp.

18. The method of claim 11, further comprising, after step (c), separating the hollow structural form and the sample vessel, and after step (d), removing the biological material from the hollow structural form.

19. The method of claim 18, wherein said removing step comprises contacting a stamp, having an opening adjoining a hollow interior, with the porous matrix, and applying pressure to the porous matrix using the stamp, whereby the biological material passes through the opening into the hollow interior of the stamp.

20. The method of claim 11, wherein in step (c) the sample liquid is separated from the hollow structural form by drawing off the sample liquid using pressure.

21. A combination of a hollow structural form, suitable for binding a biological material to a porous matrix, inserted into an elution vessel having an inner contour surface and containing an elution solution, the hollow structural form having an outer contour surface which corresponds to the inner contour surface of the elution vessel such that the outer contour surface of the hollow structural form urges against the inner contour of the elution vessel when the inner contour surface of the elution vessel and the outer contour surface of the hollow structural form are in contact, having at least one opening to permit the passing of the elution solution from the exterior of the hollow structural form to the interior of the hollow structural form, and comprising the porous matrix, the porous matrix located such that the elution solution passing through the at least one opening passes through the porous matrix to reach the interior of the hollow structural form, and a lid which allows a gas-tight seal of the hollow structural form, wherein the hollow structural form is fixed in the elution vessel such that the hollow structural form or the elution vessel must be destroyed to remove the hollow structural form from the elution vessel.

* * * * *